Figure 1:
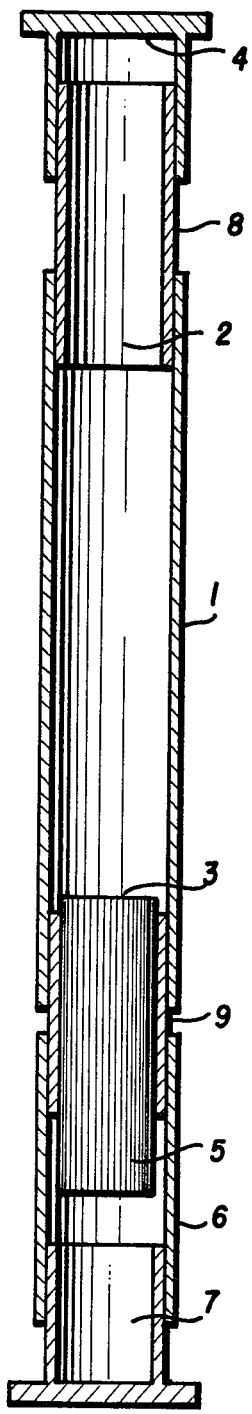

United States Patent [19]

Schlüter et al.

[11] Patent Number: 4,554,073
[45] Date of Patent: Nov. 19, 1985

[54] DEVICE FOR UPTAKE, TRANSPORTATION, AND RECOVERY OF CELL MATERIAL, AND FOR TRANSFER OF THE RECOVERED MATERIAL TO MICROSCOPE SLIDES

[75] Inventors: Gert Schlüter; Matthias Zimmermann, both of Gundelfingen, Fed. Rep. of Germany

[73] Assignee: Rhodia Aktiengesellschaft, Freiburg, Fed. Rep. of Germany

[21] Appl. No.: 587,633

[22] Filed: Mar. 8, 1984

[30] Foreign Application Priority Data

Mar. 21, 1983 [DE] Fed. Rep. of Germany ....... 3310205

[51] Int. Cl.$^4$ ............................................. B01D 27/02
[52] U.S. Cl. ................................. 210/450; 210/497.01
[58] Field of Search ............ 210/94, 450, 454, 497.01, 210/507, 508

[56] References Cited

U.S. PATENT DOCUMENTS

| | | | |
|---|---|---|---|
| 2,571,059 | 10/1951 | Puschelberg et al. | 210/507 X |
| 3,765,536 | 10/1973 | Rosenberg | 210/507 X |
| 4,157,967 | 6/1979 | Meyst et al. | 210/508 X |
| 4,179,380 | 12/1979 | Amicel et al. | 210/450 X |
| 4,400,277 | 8/1983 | Leason | 210/454 X |

FOREIGN PATENT DOCUMENTS

| | | |
|---|---|---|
| 0059403 | 9/1982 | European Pat. Off. . |
| 2244686 | 3/1974 | Fed. Rep. of Germany . |
| 2917767 | 11/1979 | Fed. Rep. of Germany . |
| 3248214 | 7/1983 | Fed. Rep. of Germany . |

*Primary Examiner*—Thomas Wyse
*Attorney, Agent, or Firm*—Stevens, Davis, Miller & Mosher

[57] ABSTRACT

A device for the uptake, transportation and recovery of cell material present in body fluids, cell-fixing liquids, and mixtures of body fluids and cell-fixing liquids, and also for the transfer of the recovered cell materials to microscope slides. The device comprises a vessel (1) with an inlet (2) and an outlet (3); a removable fiber element (5) is arranged, flush with the wall, in the outlet (3), and comprises fibers which are insoluble in body fluids and cell-fixing liquids and which are arranged lengthwise in the direction of the long axis of the vessel (1) with the formation of through capillaries, such that the capillaries have a smaller diameter than the diameter of the cells. The vessel (1) can be liquid-tightly and gas-tightly closed. Preferably, the fibers of the fiber element (5) are crimped and/or texturized fibers and/or hollow fibers.

In contrast to conventional devices and methods for the recovery of cells from cell-fixing liquids, in which the cells must be caused to sediment or settle and a long time is required, the separation of cells and cell-fixing liquids takes place in a very short time with the device according to this invention. Apart from this, the recovered cells can be directly transferred to microscope slides.

As fibers for the fiber element (5) there can be used, for example, stuffer box-crimped polypropylene fibers or cellulose-2,5-acetate fibers.

Cell-fixing liquids are, e.g., methanol, ethanol or isopropanol. Body fluids are, e.g., urine, cerebrospinal fluid, pleural effusions, or ascites.

5 Claims, 2 Drawing Figures

DEVICE FOR UPTAKE, TRANSPORTATION, AND RECOVERY OF CELL MATERIAL, AND FOR TRANSFER OF THE RECOVERED MATERIAL TO MICROSCOPE SLIDES

This invention relates to a device for the uptake, transportation and recovery of cell material present in body fluids, cell-fixing liquids, and mixtures of body fluids and cell-fixing liquids, and also for transfer of the recovered cell material to microcope slides.

In German Patent Application No. P 32 48 214.0-52, corresponding to U.S. application Ser. No. 562,852, filed Dec. 19, 1983, and to European Application No. 83 112 348.4, filed Dec. 8, 1983, applicants have proposed a device for the recovery of cell material from body fluids, consisting of a filter with a filter material arranged in a layer or several layers and insoluble in cell-fixing liquids. The device described in said German Patent Application No. P 32 48 214.0-52 is characterized in that the filter material consists of a single texturized or crimped filament yarn, the filaments of the filament yarn preferably consisting of synthetic polymers. When such a device is used, no expensive centrifugation steps are necessary, high losses of cells are avoided, and fixation of the recovered cells is possible immediately after filtration.

However, it has been found that the conventional recovery of cell material from the cell-fixing liquid has the following disadvantages:
   the cell material present in the cell-fixing liquid must first be caused to sediment or settle, which takes much time (usually at least 12 hours);
   after completion of the sedimentation process, the supernatant cell-fixing liquid must be decanted or sucked off; and
   finally, the cell sediment must still be taken up with a pipette and can only then be transferred to a microscope slide.

The object of the present invention is to make available a device for the recovery of cell material present in cell-fixing liquids, by which the described disadvantages are avoided.

This device is also useful for the takeup and transportation of cell material present in body fluids, cell-fixing liquids, and mixtures of body fluids and cell-fixing liquids, and also for the recovery of cell material present in body fluids and mixtures of body fluids and cell-fixing liquids, as well as for transfer of the recovered cell material to microscope slides.

This object is achieved in a device of the kind described above, wherein there is provided a vessel with an inlet and an outlet, in which (a) the inlet is adapted to be closed gas-tightly and liquid-tightly with a removable stopper or a removable cap;

(b) a removable fiber element is arranged flush with the wall, in the outlet, and consists of fibers insoluble in body fluids and cell-fixing liquids, the fibers being arranged lengthwise in the direction of the long axis of the vessel with the formation of through capillaries, such that the diameter of the capillaries is smaller than the diameter of the cells, the fiber element being arranged, for a portion of its length, in the outlet;

(c) the fiber element, in the other portion of its length, projects into a sleeve which, on the side on which the fiber element projects into it, has the same cross-sectional area and the same cross-section as that of the outlet, the fiber element being connected fast to the sleeve, liquid-tightly and gas-tightly; and (d) the sleeve is adapted to be closed, liquid-tightly and gas-tightly, on the side opposite the fiber element, with or by a removable stopper or a removable cap.

Advantageous embodiments of the device according to the present invention include the following features, where the fibers of the fiber element are crimped and/or texturized fibers and/or hollow fibers, and where the inlet is adapted to be liquid-tightly and gas-tightly closed with the stopper or the cap, via a sleeve which is adapted to be removed or taken away.

The advantage of feature (a) consists in that a higher capillarity, and thus a better wicking action, of the fiber element can be achieved.

The advantage of feature (b) consists in that the time required for the recovery of the cell material from the body fluid, the cell-fixing liquid, or the mixture of body fluid and cell-fixing liquid, can now be considerably shortened. That is to say, if the inlet of the vessel is closed with the stopper or the cap and the vessel is compressed transversely of its long axis, the liquid in which the cell material is present flows at an accelerated rate through the fiber element.

The advantage of feature (c) consists in that the sleeve acts as a container for the texturized or crimped filament yarn, described in the aforesaid German Patent Application No. P 32 48 214.0-52, and can thus form with it the filter mentioned there. It thereby becomes possible, when the sleeve is closed with the stopper or the cap on the side opposite the fiber element and the vessel is filled with a cell-fixing liquid, to allow the filament yarn, according to the aforesaid German Patent No. P 32 48 214.0-52, to swell out by shaking in the cell-fixing liquid, upon which the cell material adhering to the filament yarn passes over into the cell-fixing liquid.

Finally, the advantage of the feature (d) consists in that thereby the body fluid, cell-fixing liquid, or mixture of body fluid and cell-fixing liquid, is prevented from emerging from the fiber element laterally, i.e., transversely of the long axis of the vessel and hence also transversely of the long axis of the fibers of the fiber element.

For the purposes of the invention, suitable fibers for the fiber element are, for example, those consisting of:
   polyolefins, such as polypropylene;
   cellulose esters, such as cellulose-2,5-acetate;
   polyesters, such as polyethylene terephthalate; and/or
   polyamides, such as polyamide-6,6.

When crimped or texturized fibers are utilized for the fiber element, suitable candidates are those which are produced, for example, by conventional stuffer box crimping.

Body fluids in which the cell material can be present are, e.g., urine, cerebrospinal fluid, pleural effusions, or ascites.

Methanol, ethanol, or isopropanol can, for example, be utilized as cell-fixing liquids.

Figure 2:
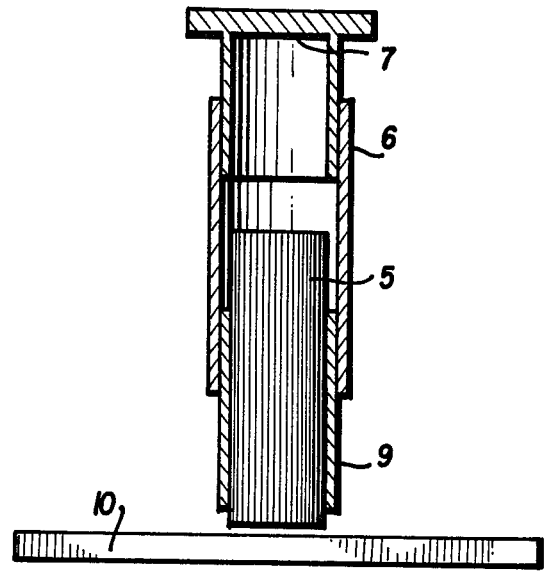

An example of a preferred embodiment of the present invention is described below in detail with reference to the accompanying drawings, in which:

FIG. 1 is a schematic resprensentation of a device according to the invention, in section through the long axis; and FIG. 2 is a schematic representation of the fiber element in the cell-transferring position, with the sleeve firmly connected to it and the stopper inserted into the sleeve on the side opposite the fiber element, also in section through the long axis.

Urine containing cells were filtered by a filter consisting of the cylindrical sleeve 8 and a filament yarn therein, according to the aforesaid German Patent Application No. P 32 48 214.0-52. After completion of the filtration process, the filter was inserted, flush with the wall, into the cylindrical vessel 1, which was held prependicularly with the inlet 2 upwards, and which contained isopropanol. The cylindrical sleeve 6 was liquid-tightly and gas-tightly closed by means of the stopper 7. The sleeve 8, with the cap 4, was then likewise liquid-tightly and gas-tightly closed. The now-closed device, according to the invention, was then shaken, upon which the filament yarn swelled and the cell material went over into the isopropanol and was simultaneously fixed.

The closed device was then sent, with the cell material and isopropanol contained in it, to a cytological laboratory. The sleeve 8, with the filament yarn and the cap 4, was there separated from the vessel 1, the vessel 1 being held perpendicularly with the inlet 2 upwards. The stopper 7 was then removed from the sleeve 6, upon which the vessel 1 with fiber element 5 was completely ventilated or opened and the isopropanol could now flow out downwardly by the capillary action of the fiber element 5. The cells were then deposited on the side of the fiber element 5 facing the inlet 2 of the vessel 1. This process of draining and settling out required a period of 30 minutes.

The fiber element 5, with the sleeve 6 connected to it by the sheath 9, was then withdrawn from the vessel 1, whereupon the cell-carrying side of the fiber element 5 was then brought into contact with a microscope slide 10 (see FIG. 2). All the cell material deposited on the fiber element 5 was transferred, by repeated contact with the microscopic slide 10, as by a stamping or tapping procedure, to the surface of the microscope slide 10.

The fiber element 5 consisted of stuffer box-crimped cellulose-2,5-acetate fibers, with a single fiber titer of 2.9 dtex and a total fiber titer of 147,000 dtex. The fibers had 22 crimps per cm, a y-shaped cross-section, and in the crimped state a length of 20 mm. The fibers were arranged such that the two ends of the fiber element 5 each possessed a plane surface. The fiber element 5 was cylindrical in shape and was surrounded with a cylindrical sheath 9 of polyethylene.

The vessel 1 was cylindrical in shape, had a length of 80 mm, an internal diameter of 12 mm, and was made of polyethylene. The vessel 1 was compressible transversely of its long axis.

The sleeve 6 was likewise cylindrical, had a length of 35 mm, an internal diameter of 12 mm, and was made of the same material as the vessel 1.

The sheath 9 of the fiber element 5 had an external diameter such that a liquid-tight and gas-tight connection was possible with both the vessel 1 and the sleeve 6. The sleeve 6 was connected firmly to the fiber element 5 by the sheath 9.

The sleeve 8 was also cylindrical, had a length of 35 mm, an internal diameter of 8 mm, and an external diameter such that a liquid-tight and gas-tight connection was possible with both the vessel 1 and the cap 4. The sleeve 8 consisted of polypropylene. The cap 4 consisted of polypropylene. The sleeve 8 could be liquid-tightly and gas-tightly closed with the cap 4.

The stopper 7 likewise consisted of polypropylene. The sleeve 6 could be liquid-tightly and gas-tightly closed with the stopper 7.

The recovered cell material consisted of cells with a diameter of $>7$ μm.

This invention has the following advantages:

By use of the device according to the invention, only a fraction of the time is required for the recovery of cell material from cell-fixing liquid than is now necessary in the conventional methods and devices for this purpose.

Decanting or sucking out the cell-fixing liquid is not necessary, since it drains out through the fiber element.

The transfer of the recovered cell material to microscope slides can immediately occur, and in fact by "stamping off", i.e., by repeated contact of the cell-carrying side of the fiber element with the surface of the microscope slide. Hence, the uptake of the cells by means of a pipette or the like is dispensed with.

Apart from this, the device according to the present invention serves not only for the recovery of cell material from cell-fixing liquids and the transfer of the cells to microscope slides, since it can also be utilized for the uptake and for transportation (for example, from the doctor's office to the cytological laboratory) of cells present in body fluids, cellfixing liquids, and mixtures of body fluids and cell-fixing liquids.

Furthermore, with the device according to this invention, cell material can also be recovered directly from body fluids and from mixtures of body fluids and cell-fixing liquids.

What is claimed is:

1. A device for takeup, transportation and recovery of cell material present in body fluids, cell-fixing liquids and mixtures of body fluids and cell-fixing liquids, and also for transfer of recovered cell material onto microscope slides, comprising a vessel with an inlet and an outlet in which
   (a) the inlet being adapted to be closed gas-tightly and liquid-tightly with a removable stopper or a removable cap;
   (b) a removable fiber element being arranged flush with the wall of the vessel, in the outlet, comprising fibers insoluble in body fluids and cell-fixing liquids, the fibers being arranged lengthwise in the direction of the longitudinal axis of the vessel with the formation of capillaries, the diameter of the capillaries being smaller than the diameter of cells of the cell material, the fiber element being arranged, for a portion of its length, in the outlet;
   (c) the fiber element, in the other portion of its length, projecting into a sleeve which, on the side on which the fiber element projects into it, has the same cross-sectional area and the same cross-section as that of the outlet, the fiber element being liquid-tightly and gas-tightly sealed to the sleeve;
   (d) the sleeve being adapted to be closed, liquid-tightly and gas-tightly, on the side opposite the fiber element, with a removable stopper or a removable cap.

2. The device according to claim 1, wherein the fibers of the fiber element being crimped and/or texturized fibers and/or hollow fibers.

3. The device according to claim 1 or 2, wherein the vessel being compressible transversely of its longitudinal axis.

4. The device according to claim 1 or 2, wherein the inlet being adapted to be liquid-tightly and gas-tightly closed with the stopper or the cap, via a sleeve being adapted to be removed or taken away.

5. The device according to claim 1 or 2, wherein the fiber element being surrounded in the region of the outlet, and in the region in which it projects into the sleeve, by a sheath which is liquid-tight and gas-tight.

* * * * *